(12) United States Patent
Suda et al.

(10) Patent No.: US 9,896,675 B2
(45) Date of Patent: Feb. 20, 2018

(54) HYPERTHERMOSTABLE ENDOGLUCANASE

(71) Applicant: HONDA MOTOR CO., LTD., Tokyo (JP)

(72) Inventors: Migiwa Suda, Kisarazu (JP); Jiro Okuma, Wako (JP); Asuka Yamaguchi, Tokyo (JP); Yoshitsugu Hirose, Wako (JP); Yasuhiro Kondo, Kawagoe (JP); Daisuke Shibata, Kisarazu (JP); Masaru Sato, Kisarazu (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/238,370

(22) Filed: Aug. 16, 2016

(65) Prior Publication Data

US 2017/0051264 A1    Feb. 23, 2017

(30) Foreign Application Priority Data

Aug. 21, 2015   (JP) .................................. 2015-163721

(51) Int. Cl.
- *C12N 9/42* (2006.01)
- *C12P 19/02* (2006.01)
- *C12P 19/14* (2006.01)

(52) U.S. Cl.
CPC ............ *C12N 9/2437* (2013.01); *C12P 19/02* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | | |
|---|---|---|---|
| 2003/0054539 A1 | 3/2003 | Schulein et al. | |
| 2003/0068805 A1 | 4/2003 | Madrid et al. | |
| 2009/0328259 A1* | 12/2009 | Harris ................ | C07K 14/5431 800/298 |

FOREIGN PATENT DOCUMENTS

| | | |
|---|---|---|
| JP | A-2010-501190 | 1/2010 |
| JP | A-2010-536391 | 12/2010 |

(Continued)

OTHER PUBLICATIONS

GenBank Accession No. AEC45566.1, published Jan. 6, 2012.*

(Continued)

*Primary Examiner* — Richard C Ekstrom
(74) *Attorney, Agent, or Firm* — Drinker Biddle & Reath LLP

(57) ABSTRACT

A hyperthermostable endoglucanase, having an endoglucanase catalytic domain including: (A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of carboxymethyl cellulose at least under conditions of 90° C. and pH 5.5, or (C) a polypeptide including an amino acid sequence having 80% or greater sequence identity with the amino acid sequence represented by SEQ ID NO: 1 or 2, and having hydrolysis activity against a substrate of carboxymethyl cellulose at least under conditions of 90° C. and pH 5.5.

8 Claims, 4 Drawing Sheets

```
AR15G-11          1 ---------------------------------MTPTAVLSPSPYPAYRAAPDGVFR  24
uncultured organism  1 MSQFSFTPPCTPAPTGSGWFLLCLLLVFLAGCAGPGAARPSPTVSVPTSAYRATPQGVFR 60

AR15G-11         25 EDQKVPLYGINWFGLETPDRAPHGLWTGRTVDFLAQMRDLGFTALRIPLSPQVLTPGYS  84
uncultured organism 61 GDEPVPLYGINWFGLETPDRAPHGLWTGRTVADFLAQMRGLGFTADRLPLSPQVLIPGRP 120

AR15G-11         85 TAMWARNSGKYPADAYEGLLYLLEEAQKADLYVLLDFHTYDPALIGGKLPGRPFGGKYTK 144
uncultured organism 121 TPSWARSAG-YPADAYEGLRYFLGEAQKVGLYVLLDFHTYDPNRIGGKLPGRPFADGYTQ 179

AR15G-11        145 EDWLIDLRRMAEIARGFPNVFGVDLCNEPHSLTWAEWKALAREGAEAVLSVNPSLWAVE 204
uncultured organism 180 ADWLADLRRMAELSREFPHIFGVDLCNEPYALTWEWKRLAREGAEAVLSVNPSVLYIVE 239

AR15G-11        205 GVGNASDYGGWSAFWGENLTEAYEDPVVLPAPFPTDRILYLPHAYGPSVYRQPYFDDSSF 264
uncultured organism 240 GVGNASDAGGNPAFWGENLAD--RQVEIAPER--SERILYLPHAYGPSVYRQPYFDAPDF 295

AR15G-11        265 PKNMPPIWEIHFGRMAGRYPLGIGEFGGRYEEDDQVWQDAFVDYLLEKQIRLFFYWSLNP 324
uncultured organism 296 PSNMPAIWDAHFGWMAGKYPLGIGEFGGRYESDDQVWQDAFADYLLAKGIRIWFYWALNP 355

AR15G-11        325 NSGDTGGVLLDDWQTVHEGKMALLRRLME-                              353
uncultured organism 356 NSGDTGGVLLDDWETVHRGKMALLRRLMGE                              385
```

(56) References Cited

FOREIGN PATENT DOCUMENTS

| JP | A-2015-136324 | 7/2015 |
|---|---|---|
| WO | WO 93/15186 A1 | 8/1993 |
| WO | WO 01/96382 A2 | 12/2001 |

OTHER PUBLICATIONS

Guo et al., "Protein tolerance to random amino acid change", Proceedings of the National Academy of Sciences USA, vol. 101, No. 25, pp. 92005-9210, 2004.*
Search Report dated Dec. 5, 2016 for European Patent Application No. 16184425.3.
Susumu Ando et al, "Hyperthermostable endoglucanase from pyrococcus horikoshii", Applied and Environmetal Microbiology, American Society for Microbiology, US, vol. 68, No. 1, Jan. 1, 2002, pp. 430-433.
Database UniProt [Online] Jun. 28, 2011, SubName: Full=Cellulose {EC0:0000313: EMBL: AEC45566. 1}; XP002764510.
Nele Ilmberger et al., "Metagenomic cellulases highly tolerant towards the presence of ionic liquids—linking thermostability and halotolerance"Applied Microbiology and Biotechnology, Springer, Berlin, DE, vol. 95, No. 1, Dec. 6, 2011, pp. 135-146.
Database EMBL [Online] May 2, 2011, "Uncultured organism fosmid cel5K cellulase precursor, gene, complete cds." XP002764511.
Tucker MP et al., "Ultra-Thermostable Cellulases from Acidothermus Cellulolyticus: Comparison of Temperature Optima with Previously Reported Cellulases", Biotechnology. The International Monthly for Industrial Biology, Nature Publishing Group, US, vol. 1, No. 8, Aug. 1, 1989, pp. 817-820.
Database EMBL [Online] Jun. 9, 2001, "Thermus caldophilus cellulose (celA) gene, complete cds," XP002764512.
Japanese Office Action dated Jan. 31, 2017 from corresponding Japanese patent application No. 2015-163721 (with attached English-language translation).
66th SBJ Annual Meeting Abstracts, 2014, p. 123, 2P-065, with English-language translation.
66th SBJ Annual Meeting Abstracts, 2014, p. 123, 2P-062, with English-language translation.
Appl. Environ. Microbiol, 1996, 62 (8), p. 3047-3049.
J. Mol. Biol., 2002, 320, p. 883-897.

* cited by examiner

FIG. 1

```
AR15G-11            1  ------------------------MTPTAVLSPSPYPAYRAAPDGVFR    24
uncultured organism 1  MSQFSFTPPCTPAPTGSGWFLLCLLLVFLAGCAGPGAARPSPTVSVPTSAYRATPQGVFR  60

AR15G-11           25  EDQKVPLYGINWFGLETPDRAPHGLWTGRTVPDFLAQMRDLGFTALRIPLSPQVLTPGYS   84
uncultured organism 61 GDEPVPLYGINWFGLETPDRAPHGLWTGRTVADFLAQMRGLGFTAIRIPLSPQVLIPGRP  120

AR15G-11           85  TANMARNSGNYPADAYEGILYLLEEAQKADLYVLLDDFHTYDPALIGGKLPGRPFGGKYTK 144
uncultured organism 121 TPSNWARSAG-YPADAYEGLRYFLGEAQKVGVLYVLLDDFHTYDPNRIGGKLPGRPFADGYTQ 179

AR15G-11          145  EDMLTDLRRMAEIARGFPNWFGVDLCNEPHSLTWAEWKALAREGAEAVLSVNPSLWAVE  204
uncultured organism 180 ADWLADLRRMAELSREFPHIFGVDLCNEPVALTWREWKRLAREGAEAVLSVNPSVLVIVE  239

AR15G-11          205  GVGNASDNGGMSAFWGENLTEAYEDPVVLPAPFPTDRILYLPHAYGPSVYRQPYFDDSSF  264
uncultured organism 240 GVGNASDAGGMPAFWGENLAD--RDVETAPER--SERILYLPHAYGPSVYRQPYFDAPDF  295

AR15G-11          265  PKNMPPIWEIHFGRMAGRYPLGIGEFGGRYEEDDQVWQDAFVDYLEKDIRLFFYWSLNP   324
uncultured organism 296 PSNMPAIMDAHFGMMAGKYPLGIGEFGGRYEGDDQVWQDAFADYLLAKGIRIMFYWALNP  355

AR15G-11          325  NSGDTGGVLLDDWQTVHEGKMALLRRLME-                               353
uncultured organism 356 NSGDTGGVLLDDWETVHRGKMALLRRLMGE                              385
```

HYPERTHERMOSTABLE ENDOGLUCANASE

BACKGROUND OF THE INVENTION

Field of the Invention

The present invention relates to a hyperthermostable endoglucanase, a polynucleotide encoding the hyperthermostable endoglucanase, an expression vector for expressing the hyperthermostable endoglucanase, a transformant into which the expression vector has been incorporated, and a method for producing a lignocellulose degradation product using the hyperthermostable endoglucanase.

Priority is claimed on Japanese Unpublished Patent Application No. 2015-163721, filed Aug. 21, 2015, the content of which is incorporated herein by reference.

SEQUENCE LISTING

The instant application contains a sequence listing which has been submitted in ASCII format via EFS-Web and is hereby incorporated by reference in its entirety. Said ASCII copy, created on Aug. 25, 2016 is named 215485_0005_ST25.txt and is 13,736 bytes in size.

Description of Related Art

In recent years, as a result of environmental problems such as global warming and atmospheric pollution, there has been considerable progress in the development of new energy sources that can be used as alternatives to fossil fuels such as solar power, wind power and geothermal power. In terms of suppressing the discharge of carbon dioxide, one technique that is attracting particular attention is the use of plant biomass, which is a renewable energy source. The main components of plant biomass are cellulose, hemicellulose and lignin. Methods of hydrolyzing plant biomass include biological methods, physical methods and chemical methods, and biological hydrolysis methods using enzymes (cellulases) are currently the most widely used. Cellulose and hemicellulose can be hydrolyzed to form monosaccharides such as glucose and xylose, which can then be used as the raw materials for biofuels or chemical products.

Lignocellulose is recalcitrant due to its highly complex structure, and is difficult to degrade and hydrolyze with a single enzyme. Accordingly, among the various polysaccharides, hydrolysis of cellulose generally requires three types of glycoside hydrolase enzymes, namely an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, the hydrolysis of hemicellulose requires a xylanase (endo-1,4-β-xylanase, EC 3.2.1.8) and a β-xylosidase (3.2.1.37).

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 80° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

Thermostable enzymes that can be used in lignocellulose hydrolysis processes at high temperature, and particularly endoglucanases that are required in the hydrolysis of cellulose, have been isolated in large numbers from thermophiles, filamentous fungi, and Archaea and the like for purposes such as lignocellulose degradation, processing agents for cellulose fibers, and pulp processing and the like (for example, see Patent Documents 1 and 2). Moreover, various attempts have also been made at improving the specific activity or thermostability of these enzymes by using mutants of the host organism or modifying a portion of the enzyme amino acid sequence. However, the vast majority of these enzymes have an optimum temperature of 60 to 80° C., and further improvements in the thermostability are still required.

RELATED ART LITERATURE

Patent Documents

Patent Document 1: U.S. Patent Application No. 2003/0054539
Patent Document 2: U.S. Patent Application No. 2003/0068805

SUMMARY OF THE INVENTION

Problems to be Solved by the Invention

The present invention has an object of providing a novel hyperthermostable endoglucanase that exhibits hydrolysis activity against a substrate of carboxymethyl cellulose (hereafter sometimes abbreviated as CMC) at least under conditions of 90° C. and pH 5.5, a polynucleotide encoding the hyperthermostable endoglucanase, an expression vector for expressing the hyperthermostable endoglucanase, a transformant into which the expression vector has been incorporated, and a method for producing a lignocellulose degradation product using the hyperthermostable endoglucanase.

Means for Solving the Problem

In order to achieve the above object, the inventors of the present invention extracted DNA directly from the high-temperature soils of hot springs, and by carrying out large-scale metagenomic sequencing of the microbial flora that was difficult to culture, they succeeded in obtaining a hyperthermostable endoglucanase having a novel amino acid sequence, thus enabling them to complete the present invention.

In other words, a hyperthermostable endoglucanase, a polynucleotide, an expression vector, a transformant, a method for producing a hyperthermostable endoglucanase, a glycoside hydrolase mixture, and a method for producing a lignocellulose degradation product according to the present invention have the aspects [1] to [8] described below.
[1] A hyperthermostable endoglucanase, having an endoglucanase catalytic domain including:
(A) a polypeptide including the amino acid sequence represented by SEQ ID NO: 1 or 2,
(B) a polypeptide including an amino acid sequence in which at least one amino acid has been deleted, substituted, or added in the amino acid sequence represented by SEQ ID NO: 1 or 2, and having hydrolysis activity against a substrate of carboxymethyl cellulose at least under conditions of 90° C. and pH 5.5, or (C) a polypeptide including an amino acid sequence having 80% or greater sequence identity with the amino acid sequence represented by SEQ. ID NO: 1 or 2, and having hydrolysis activity against a substrate of carboxymethyl cellulose at least under conditions of 90° C. and pH 5.5.

[2] A polynucleotide, having a region encoding an endoglucanase catalytic domain, the region including:

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and which has hydrolysis activity against a substrate of carboxymethyl cellulose at least under conditions of 90° C. and pH 5.5, (c) a nucleotide sequence encoding a polypeptide which includes an amino acid sequence having 80% or greater sequence identity with the amino acid sequence represented by SEQ ID NO: 1 or 2, and which has hydrolysis activity against a substrate of carboxymethyl cellulose at least under conditions of 90° C. and pH 5.5, (d) a nucleotide sequence having 80% or greater sequence identity with a nucleotide sequence represented by SEQ ID NO: 3 or 4, and encoding a polypeptide that has hydrolysis activity against a substrate of carboxymethyl cellulose at least under conditions of 90° C. and pH 5.5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of carboxymethyl cellulose at least under conditions of 90° C. and pH 5.5.

[3] An expression vector incorporating the polynucleotide according to [2], the expression vector being capable of expressing a polypeptide having endoglucanase activity in a host cell.

[4] A transformant into which the expression vector according to [3] has been introduced.

[5] The transformant according to [4], which is a eukaryote.

[6] A method for producing a hyperthermostable endoglucanase the method including generating the hyperthermostable endoglucanase in the transformant according to [4] or [5].

[7] A glycoside hydrolase mixture, including the hyperthermostable endoglucanase according to [1], a hyperthermostable endoglucanase encoded by the polynucleotide according to [2], or a hyperthermostable endoglucanase produced by the method for producing a hyperthermostable endoglucanase according to [6], and at least one other glycoside hydrolase.

[8] A method for producing a lignocellulose degradation product, the method including generating the lignocellulose degradation product by bringing a material containing lignocellulose that includes cellulose into contact with the hyperthermostable endoglucanase according to [1], a hyperthermostable endoglucanase encoded by the polynucleotide according to [2], the transformant according to [4] or [5], a hyperthermostable endoglucanase produced by the method for producing a hyperthermostable endoglucanase according to [6] or the glycoside hydrolase mixture according to [7].

Effects of the Invention

The hyperthermostable endoglucanase according to the present invention has hydrolysis activity against a substrate of CMC at least under conditions of 90° C. and pH 5.5. For this reason, the hyperthermostable endoglucanase is suitable for hydrolysis processes of materials containing lignocellulose including cellulose under high-temperature conditions.

Furthermore, the polynucleotide according to the present invention, an expression vector incorporating the polynucleotide, and a transformant into which the expression vector has been introduced can be used favorably in the production of the hyperthermostable endoglucanase according to the present invention.

BRIEF DESCRIPTION OF THE DRAWINGS

FIG. 1 is an amino acid sequence alignment diagram of the amino acid sequence (SEQ ID NO: 1) of a polypeptide encoded by an open reading frame AR15G-11 (SEQ ID NO: 3), and the amino acid sequence (SEQ ID NO: 8) of an uncultured organism (GenBank: AEC45566.1) obtained by metagenomic methods.

DETAILED DESCRIPTION OF THE INVENTION

[Hyperthermostable Endoglucanase]

Figure 2:
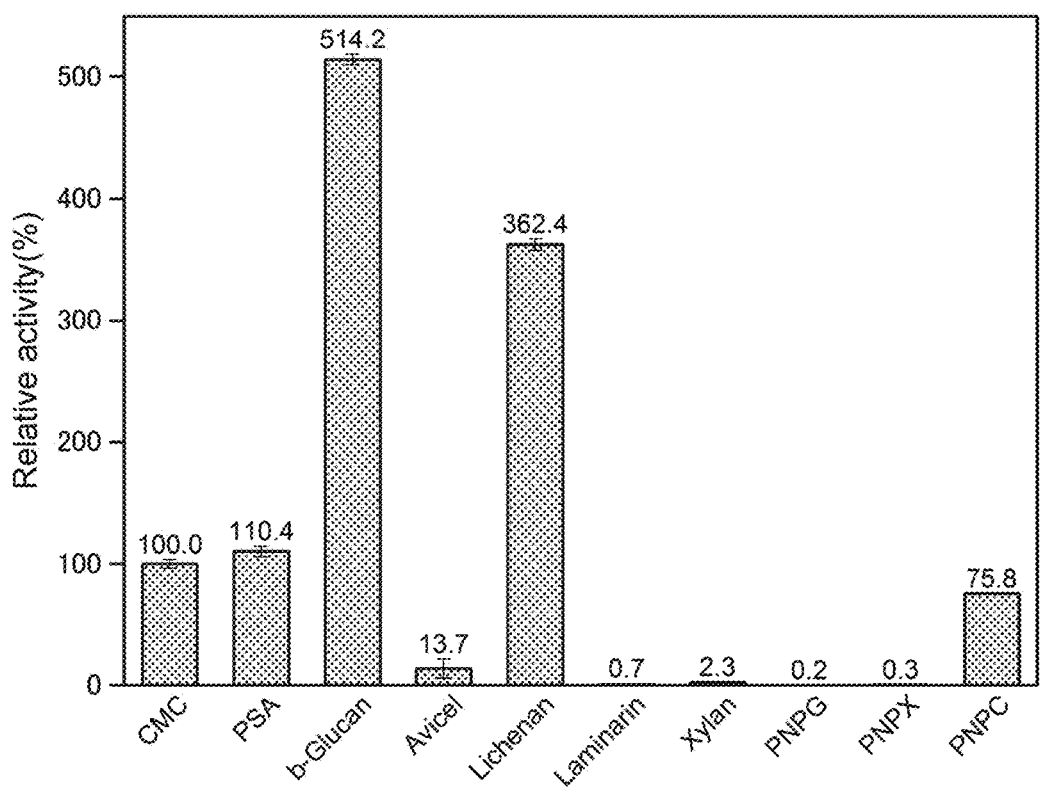
FIG. 2 is a diagram showing relative values (%) for the hydrolysis activity against various substrates of the AR15G-11-7 protein expressed in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining open reading frames (ORFs) encoding amino acid sequences similar to those of known endoglucanases (for example, amino acid sequences having 20% or higher sequence identity, and an expectation value (E-value) of less than Ie$^{-20}$). For each of the 106 ORFs for which an endoglucanase catalytic domain was confirmed, primers were designed based on the nucleotide sequence information of the ORE, and gene candidates were cloned from the metagenomic DNA of the high-temperature hot spring soil by the PCR method. The PCR-cloned DNAs were incorporated into E. coli, and proteins encoded by these nucleotide sequences were expressed and subjected to functional screening by CMC hydrolysis activity assay. Finally, a hyperthermostable endoglucanase (hereafter also referred to as "AR15G-11-7") having endoglucanase activity was obtained from the amino acid sequences encoded by these ORFs. The amino acid sequence of AR15G-11-7 is represented by SEQ ID NO: 2, and the nucleotide sequence encoding the amino acid sequence of AR15G-11-7 is represented by SEQ ID NO: 4.

As shown below in Example 1<9>, AR15G-11-7 exhibits hydrolysis activity against CMC, β-glucan, lichenan composed of a β-1,3-linked and β-1,4-linked glucan, the amorphous cellulose known as phosphoric acid swollen Avicel (PSA) and p-nitrophenyl-β-D-cellobioside (hereafter sometimes abbreviated as PNPC), but exhibits almost no hydrolysis activity against the crystalline cellulose known as Avicel, laminarin composed of a β-1,3-linked and β-1,6-linked glucan, xylan, p-nitrophenyl-β-D-xylopyranoside (hereafter sometimes abbreviated as PNPX) and p-nitrophenyl-β-D-glucopyranoside (hereafter sometimes abbreviated as PNPG).

When the amino acid sequence of AR15G-11-7 was searched against a database of known amino acid sequences, the amino acid sequence that showed the highest sequence identity was that of a cellulase uncultured organism (GenBank: AEC45566.1) (SEQ ID NO: 8) belonging to the known GH family 5, obtained by metagenomic techniques from the crater of the volcano Kamchatka, and the sequence identity (homology) with the GH5 (glycoside hydrolase family 5) catalytic domain was 76%. Based on the substrate specificity and the sequence identity of the amino acid sequence with that of known proteins, it was clear that AR15G-11-7 was a novel endoglucanase belonging to the GH5 family, AR15G-11-7 has hydrolysis activity against a substrate of CMC at least under conditions of 90° C. and pH 5.5. Actually, as shown below in Example 1 <10> and <11>, AR15G-11-7 exhibits endoglucanase activity within a broad temperature range from 40 to 100° C., and across a pH range from 5 to 8, exhibits strong endoglucanase activity within a temperature range from 70 to 100° C. and a pH range from 5 to 8, and exhibits extremely strong endoglucanase activity within a temperature range from 80 to 100° C. and a pH range from 5 to 8.

In the present description, the expression "has activity" or "exhibits activity" means that the enzyme acts against at least one substrate, causing a significant difference in the amount of reducing ends or the color development reaction of the hydrolyzed substrate compared with a negative control.

The expression "has endoglucanase activity" means that the enzyme acts against CMC at least under conditions of 90° C. and pH 5.5, causing a significant difference in the amount of reducing ends or the color development reaction of the hydrolyzed CMC compared with a negative control.

Generally, in a protein having some form of bioactivity, one or more amino acids can be deleted, substituted, or added, without impairing the bioactivity. In other words, in AR15G-11-7, one or more amino acids can be deleted, substituted, or added without impairing the glycoside hydrolase activity.

Hence the hyperthermostable endoglucanase according to the present invention is a hyperthermostable glycoside hydrolase having an endoglucanase catalytic domain including any one of the following (A) to (C):

(A) a polypeptide including the amino acid sequence represented by SEQ ID NO: 1 or 2 (namely, the polypeptide encoded by the open reading frame AR15G-11, or the polypeptide of AR15G-11-7), (B) a polypeptide including an amino acid sequence in which at least one amino acid has been deleted, substituted, or added in the amino acid sequence represented by SEQ ID NO: 1 or 2, and having hydrolysis activity against a substrate of CMC at least under conditions of 90° C. and pH 5.5, or (C) a polypeptide including an amino acid sequence having 80% or greater sequence identity with the amino acid sequence represented by SEQ ID NO: 1 or 2, and having hydrolysis activity against a substrate of CMC at least under conditions of 90° C. and pH 5.5.

In the present description, a "polypeptide in which an amino acid is deleted" means a polypeptide in which a portion of the amino acids that constitute the polypeptide is missing (removed).

In the present description, a "polypeptide in which an amino acid is substituted" means a polypeptide in which an amino acid that constitutes the polypeptide has been replaced with a different amino acid.

In the present description, a "polypeptide in which an amino acid is added" means a polypeptide in which a new amino acid has been inserted within the polypeptide.

In the above polypeptide of (B), the number of amino acids deleted, substituted, or added in the amino acid sequence represented by SEQ ID NO: 1 or 2 is preferably from 1 to 20, more preferably from 1 to 10, and still more preferably from 1 to 5. In each amino acid sequence, there are no particular limitations on the position(s) of the amino acid(s) that are deleted, substituted, or added, provided that the polypeptide including the modified amino acid sequence still has endoglucanase activity.

In the above polypeptide of (C), the sequence identity with the amino acid sequence represented by SEQ. ID NO: 1 or 2 is not specifically limited, provided it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B) and (C) may be artificially designed, or may be homologs of AR15G-11 and AR15G-11-7 or the like or partial proteins thereof.

Each of the aforementioned polypeptides of (A) to (C) may be chemically synthesized based on the amino acid sequence, or may be generated by a protein. expression system using the polynucleotide according to the present invention described below. Further, each of the polypeptides of (B) and (C) can also be artificially synthesized based on the polypeptide including the amino acid sequence represented by SEQ ID NO: 1 or 2, by using a gene recombination technique to introduce amino acid mutation(s).

Each of the polypeptides of (A) to (C) has hydrolysis activity against a substrate of CMC at least under conditions of 90° C. and 5.5. As a result, a hyperthermostable endoglucanase can be obtained by having any one of the polypeptides of (A) to (C) as the endoglucanase catalytic domain.

The hyperthermostable endoglucanase according to the present invention acts against substrates composed of least one compound selected from the group consisting of compounds having β-1,3 linkages and β-1,4 linkages, and compounds having β-1,4 linkages.

Examples of the compounds having β-1,3 linkages and β-1,4 linkages include lichenan and β-glucans. Examples of the compounds having β-1,4 linkages include crystalline celluloses such as CMC, PSA, cellobiose, Avicel, bacterial microcrystalline cellulose (hereafter sometimes abbreviated as BMCC) and filter paper.

The hyperthermostable endoglucanase according to the present invention preferably acts against at least CMC substrates, and more preferably also acts against not only CMC, but also at least one other substrate selected from the group consisting of β-glucans, lichenan, PSA and PNPC.

In addition to the substrates mentioned above, the hyperthermostable endoglucanase according to the present invention may also act against other substrates such as glucans. Examples of other compounds which can act as a substrate for the hyperthermostable endoglucanase according to the present invention include xylan, PNPX, PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside, glucans composed of β-1,3 linkages, and oligosaccharides composed of β-1,6 linkages such as gentiobiose.

The hyperthermostable endoglucanase according to the present invention exhibits CMC hydrolysis activity, at least under conditions of pH 5.5, and preferably within a temperature range from 80 to 100° C., more preferably within a temperature range from 70 to 100° C., and still more preferably within a broad temperature range from 40 to 100° C. The optimum temperature of the CMC hydrolysis activity of the hyperthermostable endoglucanase according to the present invention, under conditions at pH 5.5, is preferably within a range from 80 to 100° C.

The term "thermostable" used in relation to the thermostable endoglucanase according to the present invention means that the enzyme has endoglucanase activity within a temperature range from 40 to 100° C.

The optimum pH of the endoglucanase activity of the hyperthermostable endoglucanase according to the present invention varies depending on the reaction temperature and the substrate, but is typically within a range from pH 5.0 to 7.0. When the substrate is CMC, the optimum pH at 50° C. is 5.4. The hyperthermostable endoglucanase according to the present invention preferably exhibits endoglucanase activity at least within a range from pH 5.0 to 7.0, and more preferably exhibits endoglucanase activity within a range from pH 5.0 to 8.0.

The hyperthermostable endoglucanase according to the present invention may also have xylanase activity in addition to the endoglucanase activity. This xylanase activity of the hyperthermostable endoglucanase according to the present invention is preferably exhibited at least under conditions of 90° C. and pH 5.5.

The hyperthermostable endoglucanase according to the present invention may also have, in addition to the endoglucanase activity and xylanase activity, other glycoside hydrolase activity besides the endoglucanase activity and the xylanase activity. Examples of this other glycoside hydrolase activity include β-xylosidase activity, β-glucosidase activity or cellobiohydrolase activity.

The hyperthermostable endoglucanase according to the present invention may be an enzyme composed solely of the endoglucanase catalytic domain including any one of the aforementioned polypeptides of (A) to (C), or may be an enzyme that also includes other domains. Examples of these other domains include other domains of conventionally known glycoside hydrolases besides the enzyme catalytic domain. For example, the hyperthermostable endoglucanase according to the present invention also includes enzymes obtained by substituting the enzyme catalytic domain in a publicly known glycoside hydrolase with any of the aforementioned polypeptides of (A) to (C).

When the hyperthermostable endoglucanase according to the present invention includes one or more other domains besides the endoglucanase catalytic domain, the hyperthermostable endoglucanase preferably includes a cellulose-binding module. The cellulose-binding module may be positioned upstream (on the N-terminal side) or downstream (on the C-terminal side) of the endoglucanase catalytic domain. Further, the cellulose-binding module and the endoglucanase catalytic domain may be either bonded directly or bonded via a linker region of appropriate length. In the hyperthermostable endoglucanase according to the present invention, a cellulose-binding module preferably exists either upstream or downstream from the endoglucanase catalytic domain with a linker region positioned therebetween, and a hyperthermostable endoglucanase in which a cellulose-binding module exists upstream of the endoglucanase catalytic domain with a linker region positioned therebetween is particularly preferred.

The cellulose binding module included in the hyperthermostable endoglucanase according to the present invention may be any region having the ability to bind cellulose, such as the ability to bind PSA or crystalline Avicel, and there are no particular limitations on the amino acid sequence of the module. Examples of the cellulose-binding module include the types of cellulose-binding modules present in known proteins, and appropriately modified versions thereof. Further, in those cases where the hyperthermostable endoglucanase according to the present invention includes both the endoglucanase catalytic domain and a cellulose-binding module, it is preferable that these are bonded via a linker sequence. There are no particular limitations on the amino acid sequence or the length and the like of the linker sequence.

The hyperthermostable endoglucanase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence. When the hyperthermostable endoglucanase according to the present invention has a signal peptide at the N-terminal or C-terminal, the hyperthermostable endoglucanase expressed within a transformant can be either secreted outside the cells or localized within the endoplasmic reticulum of the cells.

Furthermore, the hyperthermostable endoglucanase according to the present invention may also have various types of tags added, for example at the N-terminal or the C-terminal of the hyperthermostable endoglucanase, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the hyperthermostable endoglucanase according to the present invention contains an endoglucanase catalytic domain including any one of the aforementioned polypeptides of (A) to (C); and also contains, according to need, at least one moiety selected from the group consisting of a cellulose-binding module positioned either upstream (on the N-terminal side) or downstream (on the C-terminal side) of the endoglucanase catalytic domain, a linker region, a signal peptide added to either the N-terminal or the C-terminal, and a tag added to either the N-terminal or the C-terminal.

[Polynucleotide Encoding Hyperthermostable Endoglucanase]

The polynucleotide according to the present invention encodes the hyperthermostable endoglucanase according to the present invention. By introducing an expression vector incorporating the polynucleotide into a host, the hyperthermostable endoglucanase can be produced by using the expression system oldie host Specifically, the polynucleotide according to the present invention is a polynucleotide having a region encoding an endoglucanase catalytic domain, the region including any one of the following nucleotide sequences (a) to (e):

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2 and which has hydrolysis activity against a substrate of CMC at least under conditions of 90° C. and pH 5.5, (c) a nucleotide sequence encoding a polypeptide which includes an amino acid sequence having 80% or greater sequence identity with the amino acid sequence represented by SEQ ID NO: 1 or 2, and which has hydrolysis activity against a substrate of CMC at least under conditions of 90° C. and pH 5.5, (d) a nucleotide sequence having 80% or greater sequence identity with a nucleotide sequence represented by SEQ ID NO: 3 or 4, and encoding a polypeptide that has hydrolysis activity against a substrate of CMC at least under conditions of 90° C. and pH 5.5, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of CMC at least under conditions of 90° C. and pH 5.5.

In the present description, a "polynucleotide in which a nucleotide is deleted" means a polynucleotide in which a portion of the nucleotides that constitute the polynucleotide is missing (removed).

In the present description, a "polynucleotide in which a nucleotide is substituted" means a polynucleotide in which a nucleotide that constitutes the polynucleotide has been replaced with a different nucleotide.

In the present description, a "polynucleotide in which a nucleotide is added" means a polynucleotide in which a new nucleotide has been inserted within the polynucleotide.

In the present description the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for a period of several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 3 or 4, or a nucleotide sequence obtained by modifying the nucleotide sequence represented by SEQ ID NO: 3 or 4 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 3 or 4 may be chemically synthesized based on the nucleotide sequence information, or may be obtained from the natural world using gene recombination techniques as either a full length gene that encodes AR15G-11-7 (hereafter sometimes referred to as the "AR15G-11-7 gene" or the "gene clone AR15G-11-7") or a partial region thereof including the endoglucanase catalytic domain (in the case of the AR15G-11-7 gene, a region encoding the partial region including the 295 amino acid residues from the tyrosine (Y) at position 32 through to the serine (S) at position 326 in SEQ ID NO: 2). The full length of the AR15G-11-7 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 3 or 4. The cDNA synthesized by a reverse transcription reaction using mRNA recovered from the sample as a template may also be used as a template. The sample from which the nucleic acid used as a template is recovered is preferably a sample collected from a high-temperature environment such as a hot spring soil.

In the aforementioned nucleotide sequence of (d), the sequence identity with the nucleotide sequence represented by SEQ ID NO: 3 or 4 is not specifically limited, provided it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b), (c) or (d) can be artificially synthesized by deleting, substituting, or adding one or a plurality of nucleotides in a polynucleotide including the nucleotide sequence represented by SEQ ID NO: 3 or 4. Further, the nucleotide sequence of (b), (c) or (d) may also be a full length sequence of a homologous gene of the AR15G-11-7 gene or a partial sequence thereof. The homologous gene of the AR15G-11-7 gene can be obtained using the types of gene recombination techniques used in obtaining homologous genes of a gene for which the nucleotide sequence is already known.

The polynucleotide according to the present invention may have only the region encoding the endoglucanase catalytic domain, or may also have, in addition to this region, one or more other regions such as a cellulose-binding module, a linker sequence, any of various types of signal peptides, or any of various types of tags or the like.

In other words, one aspect of the polynucleotide according to the present invention contains a region encoding an endoglucanase catalytic domain, the region including any one of the aforementioned nucleotide sequences of (a) to (e), and also contains, according to need, a region encoding at least one moiety selected from the group consisting of a cellulose-binding module, a linker region, a signal peptide and a tag.

[Expression Vector]

The expression vector according to the present invention incorporates the aforementioned polynucleotide according to the present invention, and is capable of expressing, in a host cell, a polypeptide having hydrolysis activity against a substrate of CMC at least under conditions of 90° C. and pH 5.5. In other words, the expression vector of the present invention is an expression vector into which the polynucleotide according to the present invention has been incorporated in a state capable of expressing the hyperthermostable endoglucanase according to the present invention. More specifically, an expression cassette composed, in order from the upstream side, of DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques. Alternatively, incorporation of the polynucleotide into the expression vector may also be performed using a commercially available expression vector preparation kit.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. The hyperthermostable endoglucanase according to the present invention can be expressed in this transformant. The host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced.

By culturing a transformant of *E. coli*, the hyperthermostable endoglucanase according to the present invention can be generated more easily and in large amounts. On the other hand, because proteins are glycosylated in eukaryotic cells, by using a transformant of a eukaryotic cell, a hyperthermostable endoglucanase can be generated which exhibits superior thermal stability to that achieved by using a transformant of a prokaryotic cell.

There are no particular limitations on the method used for preparing the transformant using the expression vector, and the types of methods typically used in the preparation of transformants can be employed. Examples of methods that can be used include a heat shock method, an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Hyperthermostable Endoglucanase]

The method for producing a hyperthermostable endoglucanase according to the present invention is a method for generating a hyperthermostable endoglucanase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the hyperthermostable endoglucanase according to the present invention can be expressed constitutively within the transformant. On the other hand, in the case of a transformant produced using a so-called expression inducible promoter to induce the expression by means of a specific compound or temperature condition or the like, the hyperthermostable endoglucanase according to the present invention can be expressed in the transformant by conducting an induction treatment suitable for the respective expression-inducing condition.

The hyperthermostable endoglucanase generated by the transformant may be used in a state where it is retained inside the transformant, or may be extracted from the transformant and purified.

The method used for extracting and purifying the hyperthermostable endoglucanase according to the present invention from the transformant is not particularly limited, provided the method does not impair the glycoside hydrolase activity of the hyperthermostable endoglucanase, and extraction can be carried out by methods commonly used for extracting polypeptides from cells or biological tissue. Examples of the method include a method in which the transformant is immersed in an appropriate extraction buffer to extract the hyperthermostable endoglucanase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, a known solid-liquid separation treatment such as a filtration method, pressurized filtration method or centrifugation treatment may be used, or the extraction buffer containing the immersed transformant may be squeezed. The hyperthermostable endoglucanase in the liquid extract can be purified by a known purification method such as a salting-out method, ultrafiltration method, or chromatography method.

If the hyperthermostable endoglucanase according to the present invention is expressed in the transformant in a state having a secretory signal peptide, then a solution containing the hyperthermostable endoglucanase can be readily obtained by culturing the transformant and then collecting the culture medium supernatant obtained by removal of the transformant from the obtained culture. Further, if the hyperthermostable endoglucanase according to the present invention has a tag such as a His tag, then the hyperthermostable endoglucanase in the liquid extract or in the culture supernatant can be easily purified by an affinity chromatography method using the tag.

In other words, the method for producing a hyperthermostable endoglucanase according to the present invention includes generating the hyperthermostable endoglucanase within the transformant according to the present invention, and also includes, according to need, extracting the hyperthermostable endoglucanase from the trans formant and purifying the hyperthermostable endoglucanase.

[Glycoside Hydrolase Mixture]

The glycoside hydrolase mixture according to the present invention includes the aforementioned hyperthermostable endoglucanase according to the present invention or a hyperthermostable endoglucanase produced by the method for producing a hyperthermostable endoglucanase according to the present invention, and at least one other glycoside hydrolase. The hyperthermostable endoglucanase produced by the aforementioned method for producing a hyperthermostable endoglucanase according to the present invention may be in a state where it is incorporated inside the transformant, or may be extracted from the transformant and purified. By using the hyperthermostable endoglucanase according to the present invention as a mixture with one or more other glycoside hydrolases in a polysaccharide hydrolysis reaction materials composed of lignocellulose containing persistent cellulose can be degraded more efficiently.

There are no particular limitations on the other glycoside hydrolase besides the aforementioned hyperthermostable endoglucanase included in the glycoside hydrolase mixture, provided it has lignocellulose hydrolysis activity. Examples of the other glycoside hydrolase besides the hyperthermostable endoglucanase included in the glycoside hydrolase mixture include hemicellulases such as xylanases and β-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the hyperthermostable endoglucanase, and is more preferably a mixture containing both a hemicellulase and an endoglucanase in addition to the hyperthermostable endoglucanase. Among the various possibilities, the glycoside hydrolase mixture according to the present invention is preferably a mixture containing at least one glycoside hydrolase selected from the group consisting of xylanases, β-xylosidases, cellobiohydrolases and β-glucosidases in addition to the hyperthermostable endoglucanase, and is more preferably a mixture containing all of a xylanase, β-xylosidase a cellobiohydrolase and a β-glucosidase in addition to the hyperthermostable endoglucanase.

The other glycoside hydrolase included in the glycoside hydrolase mixture is preferably a thermostable glycoside hydrolase having glycoside hydrolase activity at least at 90° C., and is more preferably a thermostable glycoside hydrolase having glycoside hydrolase activity at 40 to 100° C. By ensuring that all of the enzymes contained in the glycoside hydrolase mixture are thermostable (that is, have an optimum temperature for the enzymatic activity or a thermal denaturation temperature (melting temperature) for the enzyme protein of 40° C. or higher), the lignocellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material composed of lignocellulose containing cellulose, it becomes possible to conduct the lignocellulose hydrolysis reaction in a high-temperature environment in which the hydrolysis temperature is from 40 to 100° C. (namely, a high-temperature hydrolysis). With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for obtaining a lignocellulose degradation product by producing oligosaccharides by hydrolyzing a material composed of lignocellulose containing cellulose with the hyperthermostable endoglucanase according to the present invention. More specifically, the method of the present invention is a method for producing a lignocellulose degradation product containing hemicellulose or cellulose degradation products by bringing a material composed of lignocellulose containing hemicellulose or cellulose into contact with the hyperthermostable endoglucanase according to the present invention, the transformant according to the present invention, a hyperthermostable endoglucanase produced using the method for producing a hyperthermostable endoglucanase according to the present invention, or the glycoside hydrolase mixture according to the present invention.

Here, the expression "hemicellulose or cellulose degradation products" means products generated by the cleavage of glycosidic linkages within the hemicellulose or cellulose.

There are no particular limitations on the material composed of lignocellulose containing hemicellulose or cellulose, provided the material contains hemicellulose or cellulose. Specific examples of the material include cellulosic biomass such as weeds and agricultural waste materials, or used paper or the like. The material is preferably subjected to a mechanical treatment such as crushing or shredding, a chemical treatment with acid or alkali or the like, or a treatment such as immersion or dissolution in an appropriate buffer, prior to being brought into contact with the hyperthermostable endoglucanase according to the present invention.

The reaction conditions for the hydrolysis reaction of the material composed of lignocellulose containing hemicellulose or cellulose by the hyperthermostable endoglucanase according to the present invention may be any conditions under which the hyperthermostable endoglucanase exhibits endoglucanase activity. Conditions under which the hyperthermostable endoglucanase exhibits endoglucanase activity and xylanase activity are preferred. For example, the reaction is preferably conducted at a temperature of 40 to 100° C. and a pH of 5.0 to 8.0, is more preferably conducted at a temperature of 70 to 100° C. and a pH of 5.0 to 7.0, and is still more preferably conducted at a temperature of 80 to 100° C. and a pH of 5.0 to 7.0. The reaction time for the hydrolysis reaction may be adjusted appropriately with due consideration of the type, the method of pretreatment, and the amount and the like of the material supplied to the hydrolysis reaction. For example, the hydrolysis reaction may be performed for a reaction time of 10 minutes to 100 hours, but in the case of degradation of a cellulosic biomass, the hydrolysis reaction is typically performed for a reaction time of 1 to 100 hours.

In the hydrolysis reaction of the material composed of lignocellulose containing hemicellulose or cellulose, it is also preferable to use at least one other type of glycoside hydrolase in addition to the hyperthermostable endoglucanase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 90° C. and preferably at least at temperatures of 40 to 100° C. One aspect of the aforementioned method for producing a lignocellulose degradation product uses the hyperthermostable endoglucanase according to the present invention, the transformant according to the present invention, or a hyperthermostable endoglucanase produced by the method for producing a hyperthermostable endoglucanase according to the present invention, whereas another aspect of the method uses the aforementioned glycoside hydrolase mixture.

EXAMPLES

Next, the present invention is described in further detail based on a series of examples, but the present invention is in no way limited by the following examples.

[Example 1] Cloning of Novel Hyperthermostable Endoglucanase from Hot Spring Soil <1> DNA Extraction from Hot Spring Soil and Whole Genome Sequencing (WGS)

With the purpose of searching for genes of hyperthermostable endoglucanases, soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, mud and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver. 2, manufactured by Nippon Gene Co., Ltd.). Five μg of the extracted DNA was subjected to shotgun sequencing of the metagenomic DNA using a sequencer GS FLX Titanium 454 manufactured by Roche Diagnostics Ltd. The remaining DNA was used for PCR cloning of endoglucanase genes.

Metagenomic DNA sequencing of the hot spring soil sample AR15 yielded a whole genome sequence (WGS) data set having an average read length of 370 bp, a total read number of 5,419,406, and a total quantity of sequenced genomes of 2,007,725,040 bp.

<2> Assembly and Statistics of Hot Spring Metagenomic Data

For the nucleotide sequence read by the 454 sequencer, the output from the Roche 454 (sff file) was subjected to re-base calling using PyroBayes (Quinlan et al., Nature Methods, 2008 vol. 5, pp. 179 to 181), and a FASTA format sequence file and quality value file were obtained. After clipping their ends to improve the quality, the obtained sequence reads were assembled using the 454 Life Sciences assembly software Newbler version 2.3. Assembly was performed under settings including "minimum acceptable overlap match (mi)=0.9", "option: -large (for large or complex genomes, speeds up assembly but reduces accuracy)".

The total contig length of all contigs assembled to at least 100 bp totaled 118,600,846 bp, and this data set was used for cellulase gene analysis. Of the total read length of 5,419,406 reads, 4,805,640 reads were assembled into contigs having an average of at least 1,146 bp (a total of 103,508 contigs), of which the maximum contig length was 151,585 bp.

<3> Prediction of Open Reading Frames (ORFs) of Endoglucanases

Sequences having EC numbers of 3.2.1.4 (cellulase), 3.2.1.21 (β-glucosidase), 3.2.1.37 (β-xylosidase), 3.2.1.91

(cellulose 1,4-β-cellobiosidase) and 3.2.1.8 (endo-1,4-β-xylanase) were downloaded (date of access: 2011/12/9) from the UniProt database (http://www.uniprot.org/), and a proteome local database of these glycoside hydrolase genes was constructed. The annotation software Orphelia (Hoff et al., Nucleic Acids Research 2009, 37 (Web Server issue: W101 to W105) was used to predict gene regions (=open reading frames: also abbreviated as ORF) from the contig sequences obtained in the above section <2> (Orphelia option: default (model=Net 700, maxoverlap=60), Metagene option: -m). In order to extract glycoside hydrolase genes from the predicted ORFs, reference was made to the local database using BLASTP (blastall ver. 2.2.18). The option conditions for BLASTP were set such that: "Filter query sequence=false", "Expectation value (E)<1e$^{-20}$" [hereafter, default values were set such that: Cost to open a gap=-1, Cost to extended gap=-1, X dropoff value for gapped alignment=0, Threshold for extending hits=0, and Word size=default), and the hit ORF sequences were collected as the nucleotide sequences of glycoside hydrolase genes. The collected nucleotide sequences included the genes of glycoside hydrolases such as cellulases, endohemicellulases, and debranching enzymes.

<4> Glycoside Hydrolase (GH) Family Classification of Genes

Functional classification of the nucleotide sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each nucleotide sequence collected in section <3> above was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence)). Nucleotide sequences for which the coverage of the GH catalytic domain sequence was 70% or greater were counted as enzyme genes belonging to that particular family.

Based on the homology search results by BLASTP using the AR15 metagenome sequence data, 106 ORFs were predicted as being endoglucanase genes. The GH family classification results for these 106 ORFs are shown in Table 1. As shown in Table 1, from the AR15 metagenome, 13 full-length ORFs of endoglucanase genes belonging to the GH5 family, 4 full-length ORFs of endoglucanase genes belonging to the GH9 family, and 4 full-length ORFs of endoglucanase genes belonging to the GH12 family were obtained. Primers were designed for all of these full-length ORFs predicted as endoglucanase genes, and the genes were cloned from the hot spring soil metagenomic DNA by PCR. As a result, an endoglucanase gene was isolated from the open reading frame AR15G-11 having an endoglucanase gene sequence belonging to the GH12 family.

TABLE 1

|  | GH5 | GH9 | GH12 | GH48 | Other GH families | Total |
|---|---|---|---|---|---|---|
| Full-length ORFs | 13 | 4 | 4 | 0 | 40 | 61 |
| Partial length ORFs | 3 | 3 | 1 | 1 | 37 | 45 |
| Total | 16 | 7 | 5 | 1 | 77 | 106 |

<5> Open Reading Frame AR15G-11

The open reading frame AR15G-11 was a nucleotide sequence encoding a polypeptide (SEQ ID NO: 1) composed of 353 amino acid residues, and was a full-length sequence (SEQ ID NO: 3) wherein the amino acid residue at position 1 of the polypeptide was a start codon methionine (M), and the 3' end of the nucleotide sequence ended with a termination codon. Based on the sequence homology of the motif, it was predicted that the 295 amino acid residues from the tyrosine (Y) at position 32 through to the serine (S) at position 326 in the amino acid sequence encoded by the open reading frame AR15G-11 represented the GH5 catalytic domain. Further, a secretory signal was not detected by the secretory signal prediction software SignalP 4.1. The known amino acid sequence that exhibited the greatest sequence identity with the amino acid sequence encoded by the above ORF was that of a cellulase uncultured organism (GenBank: AEC45566.1) belonging to GH family 5 obtained by metagenomic techniques from the crater of the volcano Kamchatka. The homology between the two amino acid sequences calculated using the ClustalW algorithm was 76% for the GETS catalytic domain, thus confirming the above ORF as a novel sequence.

FIG. 1 shows the alignment of the amino acid sequence (SEQ ID NO: 1) of the polypeptide encoded by the open reading frame AR15G-11 and the amino acid sequence (SEQ ID NO: 8) of the cellulase uncultured organism (GenBank: AEC45566.1) belonging to GH family 5. In FIG. 1, the amino acids shown in white on black are the amino acid residues identical to both amino acid sequences, and "-" indicates a gap in a sequence.

<6> Gene Cloning from Open Reading Frame AR15G-11

Using a forward primer including a nucleotide sequence represented by SEQ ID NO: 7 (5'-CACCATGAC-CCCGACGGCTGTCCT-3': wherein four nucleotides (CACC) were added to the 5'-end of the nucleotide sequence represented by SEQ ID NO: 5, the CACC added to the 5'-end being a sequence used for vector insertion), and a reverse primer including a nucleotide sequence represented by SEQ ID NO: 6 (5'-TCACTCCATCAGGCGGCGG-3'), PCR was conducted using a hot spring soil DNA that had been amplified using a genomic DNA amplification kit (GenomiPhi V2 DNA Amplification Kit, manufactured by GE Healthcare, Inc.) as a template. The nucleotide sequence represented by SEQ ID NO: 5 is homologous (identical) with the partial sequence composed of the nucleotides from positions 1 to 20 of the nucleotide sequence represented by SEQ ID NO: 3. Further, the nucleotide sequence represented by SEQ ID NO: 6 is complementary with the partial sequence composed of the nucleotides from positions 1,044 to 1,062 of the nucleotide sequence represented by SEQ ID NO: 3. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

PCR cloning was used to obtain the gene clone AR15G-11-3 and the gene clone AR15G-11-7 from the open reading frame AR15G-11 (SEQ ID NO: 3). The nucleotide sequence (SEQ ID NO: 4) of the endoglucanase candidate gene clone AR15G-11-7 included 1,062 bp in a similar manner to the open reading frame AR15G-11 (SEQ ID NO: 3) but differed at two nucleotides. In other words, the nucleotide at position 896 was A in the open reading frame AR15G-11, but was G in the cloned AR15G-11-7 gene, and the nucleotide at position 932 was A in the open reading frame ARI5G-11, but was G in the AR15G-11-7 gene. These differences in the nucleotides at two positions were also reflected in differences in the amino acid sequences of the encoded polypeptides, so that the amino acid sequence of the open reading frame AR15G-11 (SEQ ID NO: 1) and the amino acid sequence of the endoglucanase candidate gene AR15G-11-7 (SEQ ID NO: 2) differed at two amino acid residues. Specifically, the amino acid residue at position 299 was a glutamine (Q) in the polypeptide encoded by the open reading frame ARI5G-11, but was an arginine (R) in the polypeptide encoded by the AR15G-11-7 gene, and the amino acid residue at position 311 was a glutamic acid (E) in the polypeptide encoded by the open reading frame ARI5G-11, but was a glycine (G) in the polypeptide encoded by the AR15G-11-7 gene.

<7> Gene Expression of AR15G-11-7 Gene and Purification of Enzyme Protein

Following sequence confirmation, the heat shock method was used to introduce the plasmid having the target gene into E. coli for protein expression. The Rosetta-gamiB (DE3) pLysS strain (manufactured by Merck & Co., Inc.) was used as the competent cell for the transformation. Expression of the target protein was induced by inoculating the E. coli having the target gene into an LB medium containing 100 mg/L, of ampicillin, culturing to about $OD_{600}$=0.2 to 0.8 subsequently adding IPTG (isopropyl-β-D(−)-thiogalactopyranoside), and then performing additional culturing for 20 hours. Following culturing, the E. coli was collected by centrifugation, and an amount of 50 mM Tris-HCl buffer (pH 8.0) equivalent to 1/10 of the volume of the culture medium was added and suspended. Subsequently, a process consisting of 30 seconds disrupting and then 30 seconds of rest was repeated 10 times using an ultrasonic disrupter BioRuptor UCD-200T (manufactured by Cosmo Bio Co., Ltd.), thus obtaining a crude extract of the gene recombinant E. coli containing the target protein. This gene recombinant E. coli crude extract was heated at 70° C. for 2 hours and then subjected to centrifugal separation, and the resulting supernatant was used as a crude enzyme solution.

In those cases where the enzyme protein required purification, a bacterial cell suspension obtained by performing culturing and centrifugation in the same manner as described above was subjected to 7 or 8 cycles of a process consisting of 5 minutes disrupting and then 5 minutes of rest using an ultrasonic disrupter Astrason 3000 (manufactured by MISONIX Inc.), thus obtaining a crude extract of the gene recombinant E. coli containing the target protein. This gene recombinant E. coli crude extract was then filtered through a filter (pore size φ=0.45 μm, manufactured by EMD Millipore Corporation), and the resulting filtrate was used as a gene recombinant E. coli homogeneous supernatant.

NaCl was added to the gene recombinant E. coli homogeneous supernatant to achieve a final concentration of 500 mM, the resulting mixture was loaded onto an affinity column HisTrap FF (manufactured by GE Healthcare, Inc.) equilibrated with a 50 mM Tris-HCl buffer (pH 8.0) containing 500 mM of NaCl, and a medium-high pressure liquid chromatography system AKTA design (manufactured by GE Healthcare, Inc.) was used to fractionate proteins with a concentration gradient of 0 to 100% in a 50 mM Tris-HCl buffer (pH 8.0) containing 500 mM of NaCl and 500 mM of imidazole.

The fractions exhibiting CMC hydrolysis activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with CMC hydrolysis activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting CMC hydrolysis activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting CMC hydrolysis activity were pooled, a buffer exchange to a 50 mM Tris-HCl buffer (pH 8.0) and subsequent concentration were performed using the VIVASPIN 20, and using an ion exchange column HiTrap Q HP (manufactured by GE Healthcare, Inc.), the proteins were fractionated with a concentration gradient of 0 to 50% in a 50 mM Tris-HCl buffer (pH 8.0) containing 1 M NaCl. The fractions exhibiting CMC hydrolysis activity were once again pooled, and a buffer exchange to a 50 mM Tris-HCl buffer (pH 8.0) and subsequent concentration were performed, yielding a purified enzyme with a final concentration of about 1 mg/mL.

<8> Measurement of CMC Hydrolysis Activity of AR15G-11-7

First, using CMC (carboxymethyl cellulose, manufactured by Sigma-Aldrich Co. LLC.) as a substrate, the CMC hydrolysis activity of the enzyme protein (AR15G-11-7) encoded by the AR15G-11-7 gene was investigated. In the measurements, either the crude enzyme solution obtained in section <7> above, or a purified enzyme solution prepared by diluting the purified enzyme obtained in section <7> above with a 0.05 M Tris-HCl buffer (pH 8.0) to obtain a concentration of 0.2 mg/mL was used.

Specifically, a mixed solution containing 50 μL of a 1% by mass CMC aqueous solution, 25 μL of a 200 mM acetate buffer (pH 5.5) and 25 μL of either the crude enzyme solution or the purified enzyme solution was reacted for either 10 or 15 minutes. In all measurements, a mixed solution prepared by replacing the crude enzyme solution or purified enzyme solution with a 50 mM Tris-HCl buffer (pH 8.0) and then reacting under the same conditions was used as a control. Further, the substrate solution and the mixed solution containing the buffer and the enzyme solution were held separately at the reaction temperature for five minutes (pre-incubation) before being mixed to initiate the reaction.

Following completion of the reaction, 3,5-dinitrosalicylic acid reagent (DNS solution) was added in a volume equal to that of the reaction solution, and the resulting mixture was heated at 100° C. for 5 minutes, cooled for 5 minutes on ice, and then centrifuged at 17,500 g for 5 minutes at room temperature to obtain a supernatant. The amount of reducing sugars in the supernatant was determined by measuring the absorbance at 540 nm using a spectrophotometer, calculating the amount of reducing sugars using a calibration curve prepared with glucose and then calculating the amount of reducing sugars produced by the enzymatic hydrolysis based on the difference from the control. The enzymatic activity for producing 1 μmol of reducing sugars per minute was defined as 1 U, and the value obtained by dividing this activity by the amount of protein was defined as the specific activity (U/mg). The results confirmed that both the crude enzyme solution and the purified enzyme solution had CMC hydrolysis activity.

<9> Substrate Specificity of AR15G-11-7

The hydrolysis activity of the enzyme protein (AR15G-11-7) encoded by the AR15G-11-7 gene against various cellulose substrates and hemicellulose substrates was investigated. In the measurements, the crude enzyme solution obtained in section <7> above was used. For the substrates, Avicel powder (microcrystalline cellulose powder, manufactured by Merck & Co., Inc.), PSA, CMC, barley-derived β-glucan (manufactured by Megazyme, Inc.), xylan (derived from beech wood, manufactured by Sigma-Aldrich Co. LLC.), lichenan (manufactured by MP Biomedicals, LLC), laminarin (derived from *Laminaria digitata*, manufactured by Sigma-Aldrich Co. LLC.) PNPC (manufactured by Sigma-Aldrich Co. LLC.), PNPX (manufactured by Sigma-Aldrich Co. LLC.) and PNPG (manufactured by Sigma-Aldrich Co. LLC.) were used.

The PSA was prepared by first dissolving Avicel powder (microcrystalline cellulose powder manufactured by Merck & Co., Inc.) in a phosphoric acid solution, subsequently adding sterilized distilled water to cause precipitation, and then washing until a pH of 5 or greater was obtained. The PSA used in the experiments described below was all prepared by this method.

Specifically, first, a reaction solution composed of a mixed solution containing 25 μL of a 200 mM acetate buffer (pH 5.5), 7 μL of the crude enzyme solution and 18 μL of purified water was pre-incubated at 90° C. for 5 minutes. Subsequently, 50 μL of the substrate solution (either a 1% by mass aqueous solution of Avicel powder, PSA, CMC, β-glucan xylan, lichenan or laminarin, or a 3.4 mM aqueous solution of PNPC, PNPG or PNPX) that had also been pre-incubated in the manner described above was added to the reaction solution, and the resulting mixed solution was incubated at 90° C. for 15 minutes to allow the enzyme reaction to proceed. In all measurements, a mixed solution prepared by replacing the crude enzyme solution with a 50 mM Tris-HCl buffer (pH 8.0) and then reacting under the same conditions was used as a control.

Following completion of the reaction, for those reactions where Avicel powder, PSA. CMC, xylan, lichenan or laminarin was used as the substrate, the amount of reducing sugars produced by the hydrolysis was determined in the same manner as that described above in section <8> when investigating the CMC hydrolysis activity of AR15G-11-7. However, in the case of xylan, a calibration curve prepared with xylose was used.

For the reactions where PNPG, PNPX or PNPC was used as the substrate, following completion of the reaction, an equal volume of a 200 mM aqueous solution of sodium carbonate was added to the reaction solution, and the resulting mixture was centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then calculating the amount of p-nitrophenol produced by the enzymatic hydrolysis based on the difference from the control.

Each of the above measurements was performed for three independent experiments, and a mean value and a standard error were determined. The hydrolysis activity against each substrate was calculated as a relative value (relative activity, %) relative to a value of 100% for the CMC hydrolysis activity, namely a relative value (%) for the amount of reducing sugars or amount of p-nitrophenol produced by the reaction, when the amount of reducing sugars produced by reaction using CMC as the substrate was deemed to be 100%. The relative values (%) for the hydrolysis activity against each of the substrates are shown in FIG. 2. The results revealed that AR15G-11-7 exhibited hydrolysis activity against CMC, β-glucan, PSA, lichenan and PNPC, but exhibited almost no hydrolysis activity against the other substrates.

<10> Temperature Dependency of CMC Hydrolysis Activity

The temperature dependency of the CMC hydrolysis activity of the enzyme protein (AR15G-11-7) was investigated. For the measurements, a purified enzyme solution prepared by diluting the purified enzyme obtained in section <7> above with a 0.05 M Tris-HCl buffer (pH 8.0) to 0.2 mg/mL was used.

Specifically, a mixed solution containing 25 μL of a 200 mM acetate buffer (pH 5.5), 25 μL of the purified enzyme solution and 50 μL of a 1% by mass CMC aqueous solution was reacted for 10 minutes at a temperature of 30, 40, 50, 60, 70, 80, 90 or 100° C. Following completion of the reaction, the amount of reducing sugars produced by the enzymatic hydrolysis was calculated in the same manner as that described above in section <8>. The enzymatic activity for producing 1 μmol of reducing sugars per minute was defined as 1 U, and the value obtained by dividing this activity by the amount of protein was defined as the specific activity (U/mg).

Figure 3:
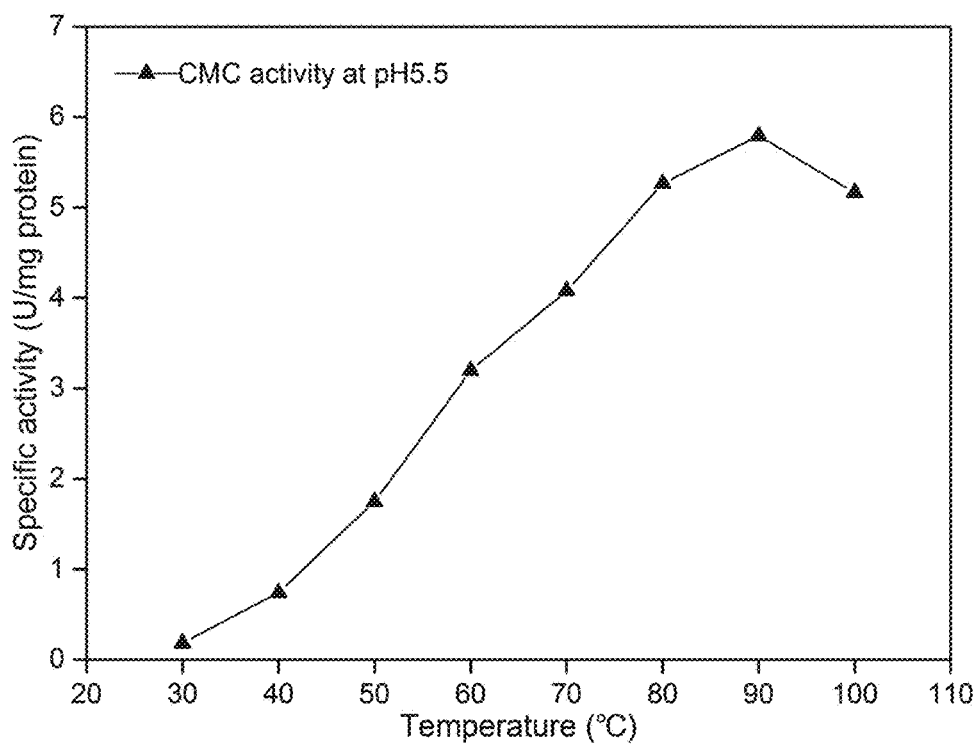
FIG. 3 is a diagram showing the CMC hydrolysis activity (pH 5.5) (U/mg protein) at various temperatures of the AR15G-11-7 protein expressed in *E. coli* in Example 1.

The results are shown in FIG. 3. AR15G-11-7 exhibited CMC hydrolysis activity in a temperature range from 40 to 100° C. The optimum temperature ($T_{opt}$) at which the highest activity was observed was 90° C. at pH 5.5.

<11> pH Dependency of CMC Hydrolysis Activity

The pH dependency of the CMC hydrolysis activity of the enzyme protein (AR15G-11-7) was investigated. For the measurements, a purified enzyme solution prepared by diluting the purified enzyme obtained in section <7> above with a 0.05 M Tris-HCl buffer (pH 8.0) to 0.2 mg/mL was used. Further, for the buffer, a 200 mM McIlvaine's buffer (MB) (pH 4.0 to 8.0), a 200 mM acetate buffer (SAB) (pH 4.0, 5.5, 6.0) or a 200 mM phosphate buffer (PB) (pH 6.0, 7.0, 8.0) was used.

Specifically, a mixed solution containing 25 μL of one of the buffers, 25 μL of the purified enzyme solution and 50 μL of a 1% by mass CMC aqueous solution was reacted at 50° C. for 10 minutes. Following completion of the reaction, the amount of reducing sugars produced by the enzymatic hydrolysis was calculated in the same manner as that described above in section <8>.

Figure 4:
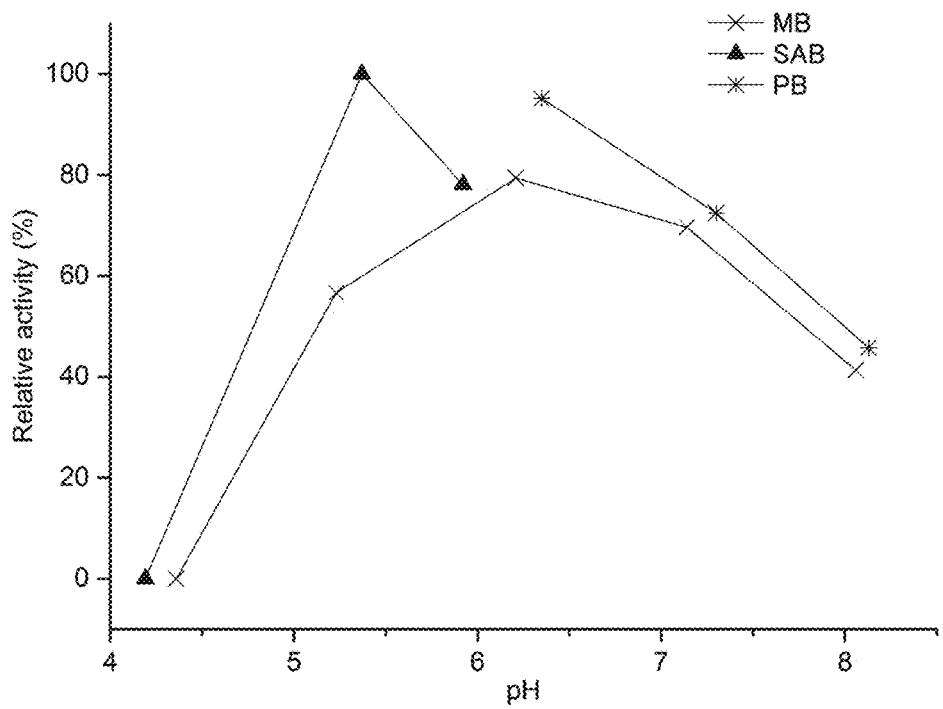
FIG. 4 is a diagram showing the CMC hydrolysis activity (50° C.) (as relative values (%) relative to a value of 100% for the hydrolysis activity at pH 5.5) at various pH values of the AR15G-11-7 protein expressed in *E. coli* in Example 1.

The CMC hydrolysis activity at each pH was calculated as a relative value (relative activity, %) relative to a value of 100% for the CMC hydrolysis activity at pH 5.5, lamely a relative value (%) for the amount of reducing sugars produced by the reaction, when the amount of reducing sugars produced by reaction at pH 5.5 was deemed to be 100%. The relative values (%) for the CMC hydrolysis activity at each of the pH levels relative to a value of 100% for the CMC hydrolysis activity at pH 5.5, are shown in FIG. 4. The actual measured values for the pH of the mixed solution of the substrate, the buffer and the enzyme were plotted.

AR15G-11-7 exhibited CMC hydrolysis activity in a range from pH 5 to 8.

The optimum pH at 50° C. was pH 5.4 (actual measured value for the mixed solution of the substrate, the buffer and the enzyme).

<12> Thermal Stability Measurement of AR15G-11-7 with CMC Substrate

In order to investigate the thermal stability (heat resistance) of the enzyme protein (AR15G-11-7), the enzyme protein was subjected to preliminary heating (pre-incubation), either at 80° C. for 0 to 168 hours, or at 90° C. for 0 to 120 minutes, and the pre-incubation time taken for the enzymatic activity to decrease to 50% of that of an untreated sample (pre-incubation time: 0 hours) (namely, the half life: $T_{half}$) was determined. The measurements used the crude enzyme solution obtained in section <7> above.

Specifically, first, a mixed solution containing 25 μL of a 200 mM acetate buffer (pH 5.5), 7 μL of the crude enzyme solution and 18 μL of purified water was pre-incubated, either at 80° C. for 0, 3, 6, 24-48, 72, 96, 121 or 168 hours, or at 90° C. for 0, 15, 30, 60 or 120 minutes. Measurement of the CMC hydrolysis activity was performed by separately heating the pre-incubated mixed solution and a 1% by mass CMC aqueous solution at 90° C. for 5 minutes, subsequently adding an equal volume of the 1% by mass CMC aqueous solution to the mixed solution, and then allowing the reaction to proceed at 90° C. for 15 minutes. Following completion of the reaction, the amount of reducing sugars produced by the enzymatic hydrolysis was determined in the same manner as that described above in section <8>. Each of the above measurements was performed for three independent experiments, and a mean value and a standard error were determined.

The CMC hydrolysis activity was calculated as a relative value (%), relative to a value of 100% for the activity of an untreated sample.

Figure 5A:
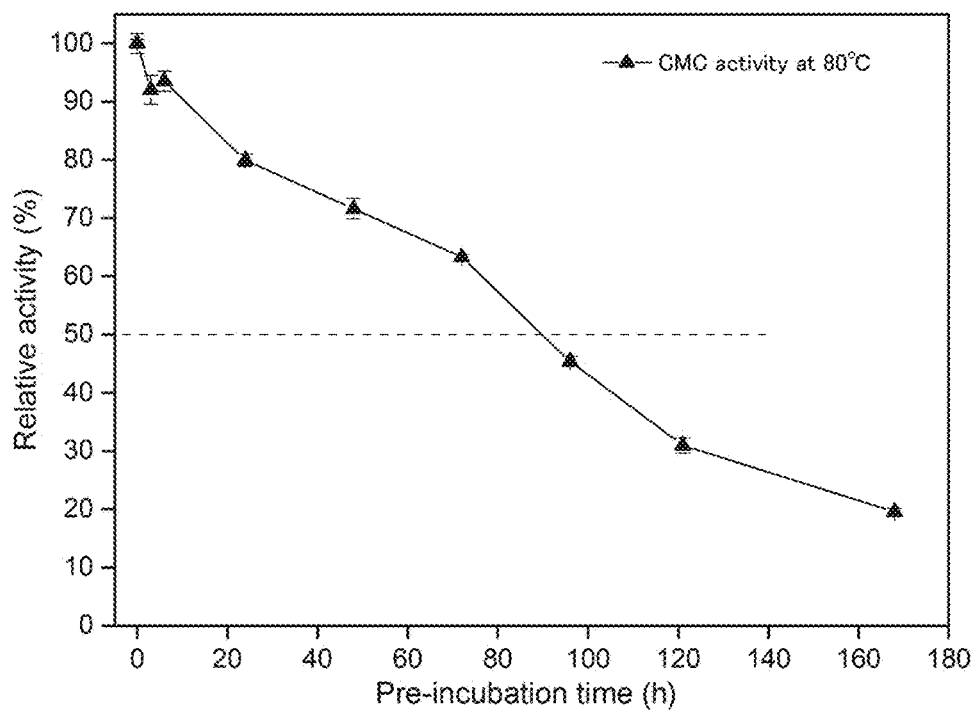
FIG. 5A is a diagram showing relative values (%) for the CMC hydrolysis activity, following various pre-incubation times at 80° C., of the AR15G-11-7 protein expressed in *E. coli* in Example 1.
Figure 5B:
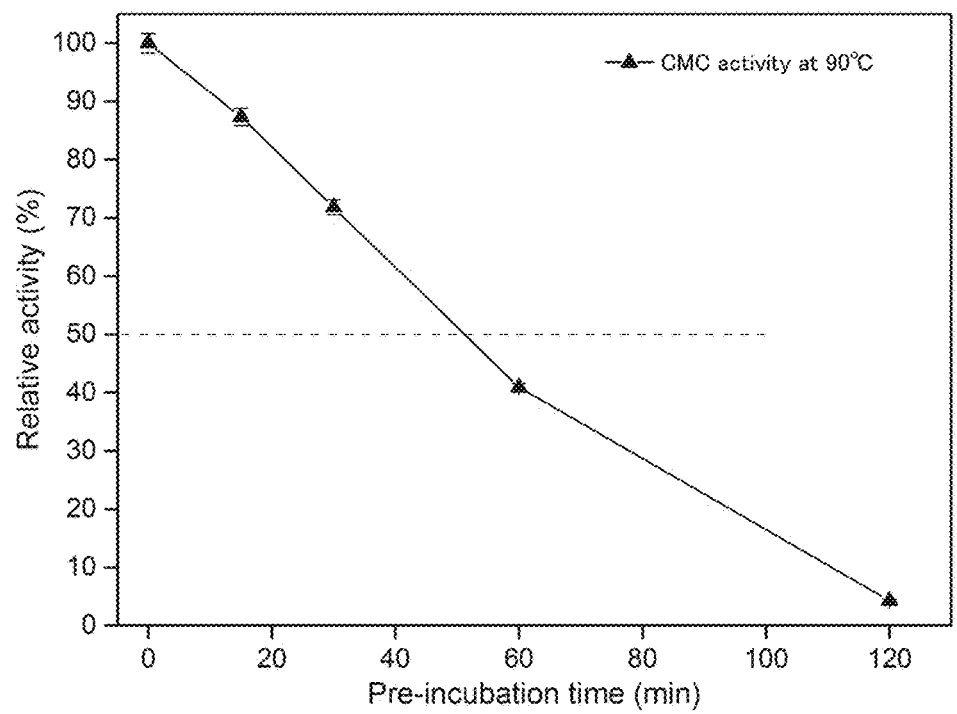
FIG. 5B is a diagram showing relative values (%) for the CMC hydrolysis activity, following various pre-incubation times at 90° C., of the AR15G-11-7 protein expressed in *E. coli* in Example 1.

The relative values (%) for the CMC hydrolysis activity at the various pre-incubation times are shown in FIG. 5. The results for the pre-incubation at 80° C. are shown in FIG. 5A, and the results for the pre-incubation at 90° C. are shown in FIG. 5B. The half life $T_{half}$ values for the AR15G-11-7 at pre-incubations temperatures of 80° C. and 90° C. were about 90 hours and about 50 minutes respectively.

The invention claimed is:

1. An isolated recombinant hyperthermostable endoglucanase, comprising:
   a polypeptide consisting of the amino acid sequence of SEQ ID NO: 1 or 2, and
   at least one moiety selected from the group consisting of a cellulose-binding module, a linker region, a signal peptide, and a tag.

2. A glycoside hydrolase mixture, comprising the hyperthermostable endoglucanase according to claim 1 and at least one other glycoside hydrolase.

3. A glycoside hydrolase mixture, comprising a hyperthermostable endoglucanase encoded by a polynucleotide and at least one other glycoside hydrolase, wherein
   the polynucleotide comprises a nucleotide sequence encoding a polypeptide comprising the amino acid sequence of SEQ ID NO: 1 or 2 and at least one moiety selected from the group consisting of a cellulose-binding module, a linker region, a signal peptide, and a tag.

4. A glycoside hydrolase mixture, comprising a hyperthermostable endoglucanase produced by a method for producing a hyperthermostable endoglucanase and at least one other glycoside hydrolase, wherein
   the method for producing the hyperthermostable endoglucanase comprises generating the hyperthermostable endoglucanase in a transformant into which an expression vector has been introduced; and
   the expression vector incorporates a polynucleotide which comprises a nucleotide sequence encoding a polypeptide comprising the amino acid sequence of SEQ ID NO: 1 or 2, and at least one moiety selected from the group consisting of a cellulose-binding module, a linker region, a signal peptide, and a tag.

5. A method for producing a lignocellulose degradation product, the method comprising generating the lignocellulose degradation product by bringing a material containing lignocellulose that includes cellulose into contact with the hyperthermostable endoglucanase according to claim 1.

6. A method for producing a lignocellulose degradation product, the method comprising generating the lignocellulose degradation product by bringing a material containing lignocellulose that includes cellulose into contact with the glycoside hydrolase mixture according to claim 2.

7. A method for producing a lignocellulose degradation product, the method comprising generating the lignocellulose degradation product by bringing a material containing lignocellulose that includes cellulose into contact with the glycoside hydrolase mixture according to claim 3.

8. A method for producing a lignocellulose degradation product, the method comprising generating the lignocellulose degradation product by bringing a material containing lignocellulose that includes cellulose into contact with the glycoside hydrolase mixture according to claim 4.

* * * * *

SEQUENCE LISTING

```
<160> NUMBER OF SEQ ID NOS: 8

<210> SEQ ID NO 1
<211> LENGTH: 353
<212> TYPE: PRT
<213> ORGANISM: Unknown
<220> FEATURE:
<223> OTHER INFORMATION: Amino acid sequence encoded by open reading
      frame AR15G-11

<400> SEQUENCE: 1

Met Thr Pro Thr Ala Val Leu Ser Pro Ser Pro Tyr Pro Ala Tyr Arg
1               5                   10                  15

Ala Ala Pro Asp Gly Val Phe Arg Glu Asp Gln Lys Val Pro Leu Tyr
            20                  25                  30

Gly Ile Asn Trp Phe Gly Leu Glu Thr Pro Asp Arg Ala Pro His Gly
        35                  40                  45

Leu Trp Thr Gly Arg Thr Val Pro Asp Phe Leu Ala Gln Met Arg Asp
    50                  55                  60

Leu Gly Phe Thr Ala Leu Arg Ile Pro Leu Ser Pro Gln Val Leu Thr
65                  70                  75                  80

Pro Gly Tyr Ser Thr Ala Asn Trp Ala Arg Asn Ser Gly Asn Tyr Pro
                85                  90                  95

Ala Asp Ala Tyr Glu Gly Leu Leu Tyr Leu Leu Glu Glu Ala Gln Lys
            100                 105                 110

Ala Asp Leu Tyr Val Leu Leu Asp Phe His Thr Tyr Asp Pro Ala Leu
        115                 120                 125

Ile Gly Gly Lys Leu Pro Gly Arg Pro Phe Gly Gly Lys Tyr Thr Lys
    130                 135                 140

Glu Asp Trp Leu Thr Asp Leu Arg Arg Met Ala Glu Ile Ala Arg Gly
145                 150                 155                 160

Phe Pro Asn Val Phe Gly Val Asp Leu Cys Asn Glu Pro His Ser Leu
                165                 170                 175
```

```
Thr Trp Ala Glu Trp Lys Ala Leu Ala Arg Glu Gly Ala Glu Ala Val
            180                 185                 190

Leu Ser Val Asn Pro Ser Leu Val Ala Val Glu Val Gly Asn
        195                 200                 205

Ala Ser Asp Asn Gly Gly Trp Ser Ala Phe Trp Gly Glu Asn Leu Thr
210                 215                 220

Glu Ala Tyr Glu Asp Pro Val Val Leu Pro Ala Pro Phe Pro Thr Asp
225                 230                 235                 240

Arg Ile Leu Tyr Leu Pro His Ala Tyr Gly Pro Ser Val Tyr Arg Gln
                245                 250                 255

Pro Tyr Phe Asp Asp Ser Ser Phe Pro Lys Asn Met Pro Pro Ile Trp
            260                 265                 270

Glu Ile His Phe Gly Arg Met Ala Gly Arg Tyr Pro Leu Gly Ile Gly
        275                 280                 285

Glu Phe Gly Gly Arg Tyr Glu Glu Asp Asp Gln Val Trp Gln Asp Ala
290                 295                 300

Phe Val Asp Tyr Leu Leu Glu Lys Asp Ile Arg Leu Phe Phe Tyr Trp
305                 310                 315                 320

Ser Leu Asn Pro Asn Ser Gly Asp Thr Gly Gly Val Leu Leu Asp Asp
                325                 330                 335

Trp Gln Thr Val His Glu Gly Lys Met Ala Leu Leu Arg Arg Leu Met
            340                 345                 350

Glu

<210> SEQ ID NO 2
<211> LENGTH: 353
<212> TYPE: PRT
<213> ORGANISM: Unknown
<220> FEATURE:
<223> OTHER INFORMATION: AR15G-11-7

<400> SEQUENCE: 2

Met Thr Pro Thr Ala Val Leu Ser Pro Ser Pro Tyr Pro Ala Tyr Arg
1               5                   10                  15

Ala Ala Pro Asp Gly Val Phe Arg Glu Asp Gln Lys Val Pro Leu Tyr
            20                  25                  30

Gly Ile Asn Trp Phe Gly Leu Glu Thr Pro Asp Arg Ala Pro His Gly
        35                  40                  45

Leu Trp Thr Gly Arg Thr Val Pro Asp Phe Leu Ala Gln Met Arg Asp
50                  55                  60

Leu Gly Phe Thr Ala Leu Arg Ile Pro Leu Ser Pro Gln Val Leu Thr
65                  70                  75                  80

Pro Gly Tyr Ser Thr Ala Asn Trp Ala Arg Asn Ser Gly Asn Tyr Pro
                85                  90                  95

Ala Asp Ala Tyr Glu Gly Leu Leu Tyr Leu Leu Glu Glu Ala Gln Lys
            100                 105                 110

Ala Asp Leu Tyr Val Leu Leu Asp Phe His Thr Tyr Asp Pro Ala Leu
        115                 120                 125

Ile Gly Gly Lys Leu Pro Gly Arg Pro Phe Gly Gly Lys Tyr Thr Lys
130                 135                 140

Glu Asp Trp Leu Thr Asp Leu Arg Arg Met Ala Glu Ile Ala Arg Gly
145                 150                 155                 160

Phe Pro Asn Val Phe Gly Val Asp Leu Cys Asn Glu Pro His Ser Leu
                165                 170                 175
```

```
Thr Trp Ala Glu Trp Lys Ala Leu Ala Arg Glu Gly Ala Glu Ala Val
            180                 185                 190

Leu Ser Val Asn Pro Ser Leu Val Val Ala Val Glu Gly Val Gly Asn
        195                 200                 205

Ala Ser Asp Asn Gly Gly Trp Ser Ala Phe Trp Gly Glu Asn Leu Thr
    210                 215                 220

Glu Ala Tyr Glu Asp Pro Val Val Leu Pro Ala Pro Phe Pro Thr Asp
225                 230                 235                 240

Arg Ile Leu Tyr Leu Pro His Ala Tyr Gly Pro Ser Val Tyr Arg Gln
                245                 250                 255

Pro Tyr Phe Asp Asp Ser Ser Phe Pro Lys Asn Met Pro Pro Ile Trp
            260                 265                 270

Glu Ile His Phe Gly Arg Met Ala Gly Arg Tyr Pro Leu Gly Ile Gly
        275                 280                 285

Glu Phe Gly Gly Arg Tyr Glu Glu Asp Asp Arg Val Trp Gln Asp Ala
    290                 295                 300

Phe Val Asp Tyr Leu Leu Gly Lys Asp Ile Arg Leu Phe Phe Tyr Trp
305                 310                 315                 320

Ser Leu Asn Pro Asn Ser Gly Asp Thr Gly Gly Val Leu Leu Asp Asp
                325                 330                 335

Trp Gln Thr Val His Glu Gly Lys Met Ala Leu Leu Arg Arg Leu Met
            340                 345                 350

Glu

<210> SEQ ID NO 3
<211> LENGTH: 1062
<212> TYPE: DNA
<213> ORGANISM: Unknown
<220> FEATURE:
<223> OTHER INFORMATION: Open reading frame AR15G-11

<400> SEQUENCE: 3
atgaccccga cggctgtcct cagtccctcc ccgtacccgg cataccgggc cgcgccggac      60
ggcgtcttcc gggaagacca gaaggtcccg ctgtacggca tcaactggtt cggcctggag     120
accccccgacc gggcccccca cggcctctgg acgggcagga ccgtcccgga cttcctggcc     180
cagatgcggg acctgggatt caccgccctg cggattcccc tctcccccca ggtcctgacc     240
cccggctatt ccactgccaa ctgggcccgg aactccggaa attaccccgc cgacgcctat     300
gaggggctcc tctacctgct tgaggaggcc caaaaggccg acctctacgt cctgctggac     360
tttcacacct acgacccggc cctcattggg gggaaactcc ccggccgccc cttcggcggc     420
aaatacacga agaagactg gctgaccgac cttcgccgga tggcggagat cgcccgcggt     480
ttccccaacg tcttcggcgt ggacctctgc aacgagcccc acagcctgac ctgggctgag     540
tggaaggcgc tggcgcggga gggagcggag gccgttctct ccgtgaaccc ctccctggtg     600
gtggccgtgg agggcgtcgg caacgcctcc gacaacgggg gctggagcgc cttctggggg     660
gaaaacctca ccgaagccta cgaggacccg gtcgtcctgc ccgccccctt cccgaccgat     720
cgcatcctct atctccccca cgcctacggc cccagcgtct accgtcagcc ctattttgac     780
gactcctcct tcccgaagaa catgcccccc atctgggaga tccacttcgg cggatggcg     840
ggccggtacc ccctgggcat cggggagttc ggaggccgct acgaggaaga cgaccaggtc     900
tggcaggacg cctttgtgga ctacctcctg gagaaagaca tcgtctcttc ttctactgg     960
tccctcaacc ccaattccgg cgacaccggc ggcgtccttc tggatgactg gcagacagtc    1020
```
cacgagggca aaatggccct cctccgccgc ctgatggagt ga                         1062

<210> SEQ ID NO 4
<211> LENGTH: 1062
<212> TYPE: DNA
<213> ORGANISM: Unknown
<220> FEATURE:
<223> OTHER INFORMATION: AR15G-11-7

<400> SEQUENCE: 4
atgaccccga cggctgtcct cagtccctcc ccgtacccgg cataccgggc cgcgccggac     60
ggcgtcttcc gggaagacca gaaggtcccg ctgtacggca tcaactggtt cggcctggag    120
accccccgacc gggccccccca cggcctctgg acgggcagga ccgtcccgga cttcctggcc    180
cagatgcggg acctgggatt caccgccctg cggattcccc tctccccccca ggtcctgacc    240
cccggctatt ccactgccaa ctgggcccgg aactccggaa attaccccgc cgacgcctat    300
gaggggctcc tctacctgct tgaggaggcc caaaaggccg acctctacgt cctgctggac    360
tttcacacct cgacccggc cctcattggg gggaaactcc ccggccgccc cttcggcggc    420
aaatacacga agaagactg gctgaccgac cttcgccgga tggcggagat cgcccgcggt    480
ttccccaacg tcttcggcgt ggacctctgc aacgagcccc acagcctgac ctgggctgag    540
tggaaggcgc tggcgcggga gggagcggag gccgttctct ccgtgaaccc ctccctggtg    600
gtggccgtgg agggcgtcgg caacgcctcc gacaacgggg gctggagcgc cttctggggg    660
gaaaacctca ccgaagccta cgaggacccg gtcgtcctgc ccgcccccctt cccgaccgat    720
cgcatcctct atctcccccca cgcctacggc cccagcgtct accgtcagcc ctattttgac    780
gactcctcct tcccgaagaa catgccccccc atctgggaga tccacttcgg gcggatggcg    840
ggccggtacc ccctgggcat cggggagttc ggaggccgct acgaggaaga cgaccgggtc    900
tggcaggacg ccttcgtgga ctacctcctg gggaaagaca tccgtctctt cttctactgg    960
tccctcaacc ccaattccgg cgacaccggc ggcgtccttc tggatgactg gcagacagtc   1020
cacgagggca aatggccct cctccgccgc ctgatggagt ga                       1062

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer.

<400> SEQUENCE: 5
atgaccccga cggctgtcct                                                 20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer.

<400> SEQUENCE: 6
tcactccatc aggcggcgg                                                  19

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer.

-continued

<400> SEQUENCE: 7
caccatgacc ccgacggctg tcct                                          24

<210> SEQ ID NO 8
<211> LENGTH: 385
<212> TYPE: PRT
<213> ORGANISM: Unknown
<220> FEATURE:
<223> OTHER INFORMATION: Uncultured organism of an environmental sample;
      GenBank Accession No. AEC45566
<220> FEATURE:
<221> NAME/KEY: MISC_FEATURE
<222> LOCATION: (1)..(385)
<223> OTHER INFORMATION: Glycoside hydrolase family 5 cellulase

<400> SEQUENCE: 8

Met Ser Gln Phe Ser Phe Thr Pro Pro Cys Thr Pro Ala Pro Thr Gly
1               5                   10                  15

Ser Gly Trp Phe Leu Leu Cys Leu Leu Leu Val Phe Leu Ala Gly Cys
            20                  25                  30

Ala Gly Pro Gly Ala Ala Arg Pro Ser Pro Thr Val Ser Val Pro Thr
        35                  40                  45

Ser Ala Tyr Arg Ala Thr Pro Gln Gly Val Phe Arg Gly Asp Glu Pro
    50                  55                  60

Val Pro Leu Tyr Gly Ile Asn Trp Phe Gly Leu Glu Thr Pro Asp Arg
65                  70                  75                  80

Ala Pro His Gly Leu Trp Thr Gly Arg Thr Val Ala Asp Phe Leu Ala
                85                  90                  95

Gln Met Arg Gly Leu Gly Phe Thr Ala Ile Arg Leu Pro Leu Ser Pro
            100                 105                 110

Gln Val Leu Ile Pro Gly Arg Pro Thr Pro Ser Trp Ala Arg Ser Ala
        115                 120                 125

Gly Tyr Pro Ala Asp Ala Tyr Glu Gly Leu Arg Tyr Phe Leu Gly Glu
    130                 135                 140

Ala Gln Lys Val Gly Leu Tyr Val Leu Leu Asp Phe His Thr Tyr Asp
145                 150                 155                 160

Pro Asn Arg Ile Gly Gly Lys Leu Pro Gly Arg Pro Phe Ala Asp Gly
                165                 170                 175

Tyr Thr Gln Ala Asp Trp Leu Ala Asp Leu Arg Arg Met Ala Glu Leu
            180                 185                 190

Ser Arg Glu Phe Pro His Ile Phe Gly Val Asp Leu Cys Asn Glu Pro
        195                 200                 205

Tyr Ala Leu Thr Trp Arg Glu Trp Lys Arg Leu Ala Arg Glu Gly Ala
    210                 215                 220

Glu Ala Val Leu Ser Val Asn Pro Ser Val Leu Val Ile Val Glu Gly
225                 230                 235                 240

Val Gly Asn Ala Ser Asp Ala Gly Gly Trp Pro Ala Phe Trp Gly Glu
                245                 250                 255

Asn Leu Ala Asp Arg Asp Val Glu Ile Ala Pro Glu Arg Ser Glu Arg
            260                 265                 270

Ile Leu Tyr Leu Pro His Ala Tyr Gly Pro Ser Val Tyr Arg Gln Pro
        275                 280                 285

Tyr Phe Asp Ala Pro Asp Phe Pro Ser Asn Met Pro Ala Ile Trp Asp
    290                 295                 300

Ala His Phe Gly Trp Met Ala Gly Lys Tyr Pro Leu Gly Ile Gly Glu
305                 310                 315                 320

-continued

```
Phe Gly Gly Arg Tyr Glu Gly Asp Asp Gln Val Trp Gln Asp Ala Phe
            325                 330                 335

Ala Asp Tyr Leu Leu Ala Lys Gly Ile Arg Ile Trp Phe Tyr Trp Ala
            340                 345                 350

Leu Asn Pro Asn Ser Gly Asp Thr Gly Gly Val Leu Leu Asp Asp Trp
        355                 360                 365

Glu Thr Val His Arg Gly Lys Met Ala Leu Leu Arg Arg Leu Met Gly
    370                 375                 380

Glu
385
```